United States Patent [19]

Schade et al.

[11] Patent Number: 5,804,395
[45] Date of Patent: Sep. 8, 1998

[54] FLUORESCENCE POLARIZATION ASSAYS OF ENZYMES AND SUBSTRATES THEREFORE

[75] Inventors: Sylvia Zottu Schade, Riverside; Michael Ernest Jolley, Round Lake, both of Ill.

[73] Assignee: The United States of America as represented by the Secretary of the Navy, Washington, D.C.

[21] Appl. No.: 566,390

[22] Filed: Dec. 1, 1995

[51] Int. Cl.[6] .................... G01N 33/573; G01N 33/53; C12Q 1/00
[52] U.S. Cl. .................. 435/7.4; 435/4; 435/7.72; 435/15; 435/24; 548/126; 548/405
[58] Field of Search ................ 435/4, 7.4, 7.72, 435/7.9, 15, 24; 548/126, 405

[56] References Cited

U.S. PATENT DOCUMENTS

| | | |
|---|---|---|
| 5,262,545 | 11/1993 | Haughland et al. ............ 435/15 |
| 5,464,767 | 11/1995 | Adamczyk et al. . |
| 5,567,596 | 10/1996 | Diamond et al. . |
| 5,571,680 | 11/1996 | Chen . |
| 5,641,633 | 6/1997 | Linn et al. . |
| 5,648,270 | 7/1997 | Kuhn et al. . |
| 5,719,031 | 2/1998 | Haugland et al. . |

FOREIGN PATENT DOCUMENTS 0194472  7/1992  European Pat. Off. .

OTHER PUBLICATIONS

Fa et al., Biochemistry, vol. 34, No. 42, 13833–13840, Oct. 1995.

*Primary Examiner*—James O. Wilson
*Attorney, Agent, or Firm*—A. D. Spevack

[57] ABSTRACT

Fluorescent-labeled substrates are provided for fluorescence polarization assays of enzymes. These substrates are proteins labeled with derivatives of BODIPY®, 4,4-difluoro-5,7-dimethyl-4-bora-3a,4a-diaza-s-indacene. The BODIPY® fluorescent tag of the present invention is pH independent, and can be used over a pH range of from about 2 to about 11. Thus one can assay, in real time, enzymes with pH maxima at pH below 7 using fluorescence polarization methodology, which could not be done with fluorescein derivatives. Different enzymes can be compared using the same BODIPY® conjugate by merely changing the buffer system which changes the pH conditions.

Fluorescence polarization assays of enzyme activity can be performed in the presence of whole bacteria and other finely suspended particles, such as might be present in tissue homogenates or cellular material. This is particularly useful for chairside assays on dental plaque or clinical assays on bacteria or tissue or exudates.

12 Claims, 5 Drawing Sheets

FLUORESCENCE POLARIZATION ASSAYS OF ENZYMES AND SUBSTRATES THEREFORE

SPECIFICATION

1. Field of the Invention

The present invention relates to rapid fluorescence polarization assays for proteolytic or hydrolytic enzyme activities. The assays could be helpful in studying the kinetics of purified enzymes and/or in quantitating bacterial or tissue proteolytic or hydrolytic enzyme activity, even in the presence of whole bacteria or fine tissue suspension.

2. Background of the Invention

Certain species of gram negative oral bacteria, including *Porphyromonas gingivalis* (*Bacteroides gingivalis*) and *Treponema denticola*, have been implicated in the etiology and pathogenesis of periodontal disease (Simonson L G, et al, J Periodontol 63, 270–273 (1992)). These microorganisms possess proteolytic and hydrolytic enzymes similar to known enzymes, such as collagenase, neuraminidase, fibrinolysin, trypsin and others. *P. gingivalis* has a potent thiol lysyl proteinase that cleaves kininogens and fibrinogen which may lead to bleeding in periodontal disease (Scott C F, et al, J Biol Chem 268, 7935–7942 (1993)). *T. denticola* has several active proteases (Rosen G, et al, Infect Immun 62,1749–1752 (1994)), one of which is on its bacterial surface (Grenier D, et al, Infect Immun 172, 347–351 (1990)), and possesses the ability to cleave immunoglobulins (Makinen P-L, et al, Infect Immun 62,4938–4947 (1994)). Several other pathogenic destructive microorganisms, such as the yeast *Candida albicans*, involved in oral thrush, or *Vibrio cholera*, the cause of dysentery, depend at least in part for pathogenicity upon proteolytic enzymes (Hase CC and Finkelstein R A, Microbiol Revs 57, 823–837 (1993)).

Heretofore there has not been a rapid method of assaying for microbial proteolytic enzymes directly on their large substrates, particularly in the presence of the microorganisms or of the tissue in which they are found. It has been cumbersome and time-consuming to use current methods to determine proteolytic activity as an index of the presence of certain microorganisms.

Convenient instrumentation for kinetic measurements using fluorescence polarization technology has recently become available, which may provide a way to measure proteases or other hydrolytic enzymes in real-time on large substrates. Fluorescence polarization has previously been used for immunoassays (Dandliker W B and Feigen G A, Biochem Biophys Res Comm 5, 299–304 (1961)) and applied to the determination of drug levels in human plasma (Jolley M E, J Anal Toxicol 5,236–240 (1981)). These methods are used for drug level determinations in hospitals throughout the world. Fluorescence polarization techniques are based on the principle that a fluorescently labeled compound, when excited by plane polarized light, will emit polarized fluorescent light. The fluorescence polarization depends on the molecular weight of the whole tagged molecular substrate, the tagged molecular complex and/or tagged fragments. Take as an example the case in which a fluorescent label is attached to the drug in a drug-antibody complex. When the high molecular weight fluorescent-drug-antibody complex is excited with plane polarized light, the emitted light remains highly polarized because the molecular complex containing the fluorophore is constrained from rotating between the time light is absorbed and emitted. When the much lower molecular weight fluorescent-drug is free in solution (not bound to an antibody) and is excited by plane polarized light, its rotation is much faster than the corresponding fluorescent-drug-antibody complex and the labeled molecules become more randomly oriented during the time the light is absorbed and emitted, so that the emitted light is much less polarized. Addition of unlabeled drug to the fluorescent-drug-antibody complex will displace the fluorescent-drug and the fluorescence polarization will drop. Thus, fluorescence polarization has been used to provide a quantitative means for measuring the amount of fluorescent-drug-antibody complex remaining in a competitive binding immunoassay. From calculations based on a standard curve, one deduces the quantity of the added competing unlabeled drug.

Fluorescence polarization immunoassays using fluorescein derivatives are disclosed in the following patents:

Wang et al, U.S. Pat. No. 4,420,568
Wang et al, U.S. Pat. No. 4,492,762
Wang et al, U.S. Pat. No. 4,585,862
Wang et al, U.S. Pat. No. 4,593,089
Wang et al, U.S. Pat. No. 4,668,640

Protease assays using a fluorescein-tagged protein substrate (abbreviated FITC-α-casein or FTC-casein) were developed by Spencer et al (Spencer R D et al, Clin Chem 19,838–844 (1973)), by Maeda et al (Maeda H, et al, Anal Biochem 92, 222–227 (1979)) and by Bolger and Checovich (Bolger B and Checovich W, BioTechniques 17, 585–589 (1994)) for use in fluorescence polarization instruments to assay several purified proteolytic enzymes. Fluorescein-labeled substrates have often been used in enzyme assays where either fluorescence intensity or fluorescence polarization technology has been used. Unfortunately, fluorescein-labeled proteins have the drawback that fluorescein loses its fluorescence property at pH 6 and below. The fluorescence is diminished even at pH 7, a common pH for measuring many enzymes. In fact, some enzymes require pH levels too low to allow the use of fluorescein derivatives heretofore known.

Haugland et al, U.S. Pat. No. 4,774,339, disclose fluorescent dyes based on the dipyrrometheneboron difluoride structure which are said to be substitutes for fluorescein because of their similarity in light absorption and emission characteristics, but do not show appreciable sensitivity to pH. The compounds are said to be capable of chemical bonding to functional groups in biomolecules such as amines, thiols, alcohols, carboxylic acids, aldehydes, and ketones. However, there is no indication that these compounds can be used in enzyme assays or in fluorescence polarization assays, but merely as tracers.

Haugland et al, U.S. Pat. Nos. 5,364,764, and 5,262,545, disclose fluorescent compounds useful in the determination of chloramphenicol acetyltransferase (CAT) enzyme activity. The compounds are fluorescent derivatives related in structure to chloramphenicol and are acylated in the presence of CAT to produce fluorescent mono- and diacetylated products which are then separated from the reaction mixture and quantitated by means of their fluorescence and/or absorbance. Among the fluorescent molecules which can be so conjugated are derivatives of fluorescein and dipyrrometheneboron difluoride.

Brinkley et al, U.S. Pat. No. 5,326,692, disclose microparticles incorporating a series of two or more fluorescent dyes having overlapping excitation and emission spectra which transfer energy through the dyes in the series which is re-emitted as an optical signal at the emission wavelength of the last dye in the series, resulting in a Stokes shift which is controlled through selection of appropriate dyes. Among the fluorescent dyes that can be used are derivatives of dipyrromethenboron difluoride.

Kang et al, U.S. Pat. No. 5,274,113, disclose derivatives of dipyrromethenboron difluoride fluorescent dyes which are chemically reactive with proteins and other biologically derived or synthetic chemical materials. At least one of the substituents on the heterocyclic fused ring is a reactive functional group, and at least one of the substituents contains a bathochromic moiety which is an unsaturated organic group, preferably heteroaryl or alkenyl. The dye-conjugated ligands described herein are useful as tools for the detection, identification and measurement of biological compounds, particularly immunochemical reaction components. There is no disclosure at all of using these compounds in fluorescence polarization assays.

Haugland et al, U.S. Pat. No. 5,248,782, disclose 4,4-difluoro-4-bora-3a,4a-diaza-s-indacenes containing heteroaryl substituents conjugated to the fluorophore. These dyes have absorption and emission spectra which are shifted to significantly longer wavelengths as compared to those of the parent dyes.

Kang et al, U.S. Pat. No. 5,187,288, disclose ethenyl-substituted derivatives of dipyrromethenboron difluoride dyes that have an absorption maximum at wavelengths longer than about 525 nm. These dyes can be used in combination with other fluorescent dyes so that the fluorescence of both compounds can be selectively excited and detected.

If one uses fluorescein derivatives to measure protease activity in fluorescence polarization methodology at pH 6 or lower, one way to circumvent this problem is to conduct the reaction in a small volume at the appropriate pH value, then dilute an aliquot into a buffer at pH 8.8 (Bolger and Checovich, BioTechniques 17, 585–587 (1994)). The buffer must be of higher buffer capacity to overcome the low pH buffer used. This dilution procedure must be carried out in a separate tube for each time point desired and requires manually timed intervals in the assay and hence there is less precision. It would be desirable to have more versatile fluorescent substrates available to allow one to detect proteolytic or hydrolytic activity in real-time. These would be ideal to use in the new instruments which automatically measure fluorescence polarization at precisely-timed intervals.

Most enzyme assays in use today that measure protease activity on large peptides or proteins as substrates are performed with cumbersome techniques. These commonly include determination by acid precipitation 1) of radioactively labeled proteins followed by radioactive counting, 2) of unlabeled proteins followed by spectrophotometric analysis or 3) of fluorescein-labeled proteins followed by spectrofluorometric readings (Twining S S, Anal Biochem 143, 30–34 (1984)). Alternatively, measurements can be made by gel electrophoresis followed by densitometer tracings or one may utilize visual inspection of clearing around bacterial colonies on agar plates. All these determinations require several manipulations and several hours or days to perform. Some are much less sensitive as well.

SUMMARY OF THE INVENTION

It is an object of the present invention to overcome the deficiencies of the prior art.

It is another object of the present invention to provide a method for determining the presence of proteolytic or hydrolytic enzymatic activity which might be due to enzymes from, in or on microorganisms, bodily fluids, or other host tissues in a clinical setting. (Microorganisms include bacteria, yeasts, fungi and others).

It is a further object of the present invention to provide an enzyme assay measured by change in fluorescence polarization useful over a wide range of pH values.

According to the present invention, fluorescent-labeled substrates are provided for fluorescence polarization assays of enzymes. These substrates are proteins labeled with 4,4-difluoro-5,7-dimethyl-4bora-3a,4a-diaza-s-indacene-3-propionic acid, succinimidyl ester (BODIPY® FL C3-SE). Other biological compounds, such as lipoproteins, glycoproteins, DNA, RNA and oligonucleotides, as well as other proteins, can be labeled with BODIPY®. Other derivatives of BODIPY® can be used as well.

The following patents describe fluorescence polarization assay in detail, and are hereby incorporated in the entirety by reference:

Wang et al, U.S. Pat. No. 4,420,568
Wang et al, U.S. Pat. No. 4,492,762
Wang et al, U.S. Pat. No. 4,585,862
Wang et al, U.S. Pat. No. 4,593,089
Wang et al, U.S. Pat. No. 4,668,640

The BODIPY® fluorescent tag of the present invention is pH independent, and can be used over a pH range from at least a minimum pH of 2 to at least a maximum pH of 11. Thus one can assay, in real-time, enzymes with pH maxima well below pH 7 using fluorescence polarization methodology, which could not be done with fluorescein derivatives. Different enzymes can be compared using the same BODIPY® conjugate by merely changing the buffer system which changes the pH conditions. In some cases, specificity may be obtained by labeling a specific substrate with BODIPY®. For example, a preparation of BODIPY®-collagen can be used as a substrate for collagenase. BODIPY®-fibrinogen and BODIPY®-plasminogen can be used in the same manner that Kinoshita, et al (Kinoshita K, et al, Anal Biochem 104, 15–22 (1980)) used fluorescein-fibrinogen and fluorescein-plasminogen to assay for plasminogen and urokinase, respectively.

Fluorescence polarization assays of enzyme activity can be performed in the presence of whole bacteria (Schade S Z, et al, J Dent Res 73, 248 (1994), abstract #1168) and other finely suspended particles, such as might be present in tissue extracts, homogenates or cellular material. This is particularly useful for chairside assays on dental plaque, which consists mainly of bacteria, or for other clinical assays on bacterial cultures, tissue exudates, homogenates or on cellular material.

BRIEF DESCRIPTIONS OF THE DRAWINGS

FIG. 1. Characteristics of BODIPY®-α-casein conjugates tested as protease substrates using trypsin. The BODIPY®-α-casein conjugates #1, #2, #3 and #4, resulted from the reaction of 1.0, 0.10, 0.01 and 0.001 mg/ml BODIPY®, respectively, with 10 mg/ml α-casein at room temperature. Each conjugate was tested at 37° C. in PBS pH 7.4 with the proteolytic enzyme trypsin at 0.5 µg/ml (5 BAEE units/ml) using fluorescence polarization methodology. Data was recorded in mP, millipolarization units. The final protease assay volume of 2.00 ml contained 0.75 µg/ml BODIPY®-α-casein (37 pmol/ml). In the legend on the graph, a-casein stands for α-casein, a protein with a molecular weight of about 20,000 daltons.

FIG. 2. Protease activity of pepsin. Chromatographically purified, crystallized pepsin was assayed at 37° C. in 0.01N HCl pH 2 using 0.5 μg/ml (25 pmoles/ml) BODIPY®-casein conjugate #5 as a substrate. Proteolytic activity was followed by automatically recording the fluorescence polarization (mP). One ng of pepsin equals 4 milliunits.

FIG. 3. Protease activity of activated papain. Protease was assayed by fluorescence polarization with 0.5 μg/ml BODIPY®-α-casein conjugate #5 in 0.1M citrate buffer pH 6 at 37° C. Ten ng papain equals 0.24 milliunits FIG. 4. Protease activity of proteinase K. Proteinase K was assayed with 0.5 μg/ml BODIPY®-α-casein conjugate #5 in PBS-azide pH 7.4 at 37° C. Ten ng equals 0.32 milliunits proteinase K.

FIG. 5. Protease activity of trypsin. Trypsin was assayed in PBS-azide pH 7.4 using 0.5 μg/ml BODIPY®-α-casein conjugate #5. Fluorescence polarization was measured in at 37° C. and recorded in mP units. One ng equals 10 milliunits BAEE.

FIG. 6. Protease activity of *Streptomyces griseus* alkaline protease. *S. griseus* alkaline protease was assayed using 0.5 μg/ml BODIPY®-α-casein #5 in 0.1M CAPS pH 11 buffer at 37° C. by fluorescence polarization. One μg equals 20 milliunits of enzyme.

FIG. 7. Dependence of protease activity of activated papain upon pH. The protease activity was measured by fluorescence polarization at 37° C. using BODIPY®-α-casein as substrate. A separate kinetic curve was performed as above for each pH value, and the change in fluorescence polarization during the first minute after addition of enzyme was plotted against pH.

FIG. 8. Protease activity of a growing culture of *T. denticola* ATCC 35405, using two different quantities of bacteria, one twice that of the other.

FIG. 9. Protease activity of a young growing culture of *P. gingivalis* ATCC 33277. Wilkins-Chalgren broth(WC) alone and filtered *P. gingivalis* culture were also tested.

DETAILED DESCRIPTION OF THE INVENTION

Figure 1:
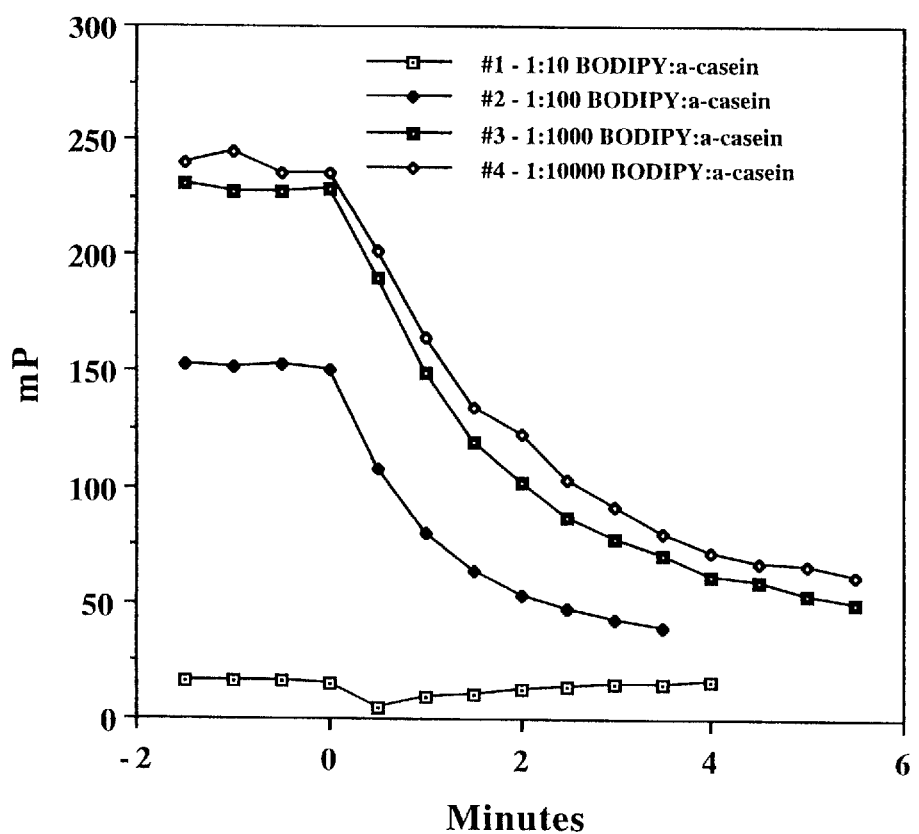

The labels of the present invention comprise BODIPY® derivatives conjugated to a substrate for the enzyme to be determined. The BODIPY® is conjugated to the substrate for the enzyme of interest. One skilled in the art can readily determine what substrate(s) to use with each enzyme of interest with a minimum of experimentation.

To determine proteolytic activity, for example, α-casein was conjugated to BODIPY® and used at four different pH values to determine the proteolytic activity of pepsin at pH 2, or activated papain at pH 6, or trypsin at pH 7.4, or proteinase K at pH 7.4 or *Streptomyces griseus* alkaline protease at pH 11.

The BODIPY®-α-casein was cleaved by pepsin in 3 minutes at a sensitivity of 1 ng/ml (4 milliunits/ml; 8 milliunits/assay) at pH 2. It was cleaved by papain in 3 minutes at a sensitivity of 20 ng/ml (0.5 milliunits/ml; 1 milliunit/assay)at pH 6. It was cleaved by trypsin in 3 minutes at a sensitivity of 5 ng/ml (50 milliunits/ml; 100 milliunits/assay) at pH 7.4. It was cleaved by proteinase K in 3 minutes at a sensitivity of 10 ng/ml (0.3 milli-units/ml; 0.6 milli-units/assay) at pH 7.4. It was cleaved by *S. griseus* protease in 3 minutes at a sensitivity of 50 ng/ml (1 milliunit/ml; 2 milliunits/assay) at pH 11.

Pepsin is a stomach enzyme whose natural environment is pH 2. Papain is an enzyme found in acidic fruit. These enzymes heretofore have not been assayed as rapidly, even using fluorescence polarization (See Bolger and Checovich).

Trypsin is a pancreatic protease; proteinase K is from a thermal vent organism and alkaline protease is from the mold, *S. griseus*.

A protein can be conjugated with BODIPY® to prepare a labeled substrate for enzyme analysis using fluorescence polarization. The diagnosis of, contraction or progress or incidence of disease, such as periodontal disease, can be readily and promptly carried out by reacting a quantity of BODIPY®-α-casein with a specimen such as dental plaque, gingival crevicular fluid, saliva, tissue extract or exudate, and determining the extent of enzymatic hydrolysis using fluorescence polarization techniques and instrumentation. A correlation of trypsin-like activity in subgingival dental plaque and incidence of severe periodontal disease has been established using other proteolytic assay methods (Schmidt E F, et al, J Dent Res 67,1505–1509 (1988)). It is anticipated that proteolytic activity assayed by the rapid fluorescence polarization method would also correlate.

ASSAY FOR ENZYMES

In accordance with the method of the present invention, a sample containing the enzyme to be determined is intermixed with a substrate for the enzyme of interest, which substrate has previously been labeled with BODIPY®. Proteins may contain more than one fluorescent BODIPY® label per molecule, depending upon the number and availability of amino acid lysines plus any unblocked amino-terminal amino acids in the protein. The degree of labeling depends also on the conditions used in the labeling reaction. The enzyme present in the sample, which may result from a purified enzyme or from the presence of a bacterium or other source of interest (tissue, exudate or the like), hydrolyzes the labeled substrate, releasing smaller fragments of the BODIPY®-labeled substrate. Upon exciting the mixture with plane polarized light of appropriate wavelength, the polarization of the fluorescence emitted over time will change. As the substrate is cleaved, smaller fragments containing BODIPY® will be produced and fewer large BODIPY®-labeled substrate molecules will be present. The decrease in the molecular weight of the of the labeled molecules results in a decrease in fluorescence polarization. The fluorescence polarization will drop with time. By measuring the initial decrease in fluorescence polarization, one can thus quantitatively determine the protease activity of an enzyme, of a bacterial culture or of a tissue.

In theory, the fluorescence polarization of free BODIPY®, i.e., not conjugated to a substrate, is low, approaching zero. Upon conjugation with a protein substrate, the BODIPY®-labeled substrate thus formed assumes the rotation of the much larger substrate molecule. The rotation is slower than that of the free BODIPY® molecule and the fluorescence polarization observed is much higher. Therefore, as an enzyme hydrolyzes a labeled substrate, the molecular weight of the substrate fragments still conjugated to BODIPY® becomes smaller and the polarization value of the solution decreases. By sequentially exciting the reaction mixture of an enzyme to be determined and a BODIPY®-labeled substrate with vertically and then horizontally polarized light and analyzing only the vertical component of the emitted light, the fluorescence polarization in the reaction mix may be accurately determined. The precise relationship between the fluorescence polarization and the concentration of the enzyme to be determined is established by measuring the change in fluorescence polarization values with known enzyme concentrations. The concentration of an enzyme can be extrapolated from a standard curve prepared with various concentrations of the enzymes.

The pH of the reaction mixture must be that at which the enzyme acts on the particular labeled substrate. As BODIPY® fluoresces at pH values ranging from about 2 to about 11, a pH can be chosen that depends on the enzyme to be determined, rather than on the fluorescence activity of the BODIPY®. Various buffers may be used to achieve and maintain the appropriate pH during the assay procedure. The particular buffer used is not critical to the present invention, but in an individual assay, a specific buffer may be preferred or needed in view of the enzyme used. Representative buffers include borate, phosphate, carbonate, citrate, tris, the "Good" buffers such as HEPES and CAPS, barbital and the like.

Assays according to the present invention can be conducted at moderate temperatures, and preferably at a constant temperature. The temperature will normally range from about 0° to 50° C., and more usually from about 15° to about 40° C.

The concentration of enzyme which can be assayed will generally vary from about $10^{-2}$ to about $10^{-13}$M, more usually from about $10^4$ to about $10^{-10}$M. Higher concentrations of enzyme may be assayed upon dilution of the original sample.

In addition to the concentration range of enzyme of interest, considerations such as whether the assay is qualitative, semiquantitative or quantitative, the equipment employed, and the characteristics of the enzyme will normally determine the concentration of BODIPY®-labeled substrate to be used. Normally to optimize the sensitivity of the assay, individual reagent concentrations will be determined empirically. Concentrations of the labeled substrate are readily ascertained by one of ordinary skill in the art without undue experimentation.

All living organisms possess proteolytic enzymes. As for disease microorganisms that use proteolytic activity as a major virulence factor, often, it is a matter of the degree of activity of one protease that gives these microorganisms the edge over their competitors.

Alternatively, the possession of a protease that performs a specific job, such as an immunoglobulin A protease, causes a breakdown of the first line of host defense preventing for example a bacterium from being phagocytized by the host immune cells. An immunoglobulin A protease (IgA protease) could be assayed more specifically perhaps by preparing BODIPY®-IgA, but BODIPY®-α-casein might be perfectly satisfactory to detect the activity.

*Candida albicans* yeast virulence is dependent upon proteolytic activity (Odds F C, Am Soc Microbiol News 60,313–318 (1994); Agabian N, et al, J Med Vet Mycology 32, 229–237 (1994)).

The virulent bacterium, *Vibrio cholerae*, which causes dysentery, possesses a potent hemagglutinin which turned out to be a protease (Hase C C and Finkelstein R A, Microbiol Rev 823–837 (1993)).

Even invasive tumor cells of higher organisms express a gelatinase A (type-IV collagenase) on the surface of their cells. This collagenase is believed to be crucial for invasion and metastasis (Sato H, et al, Nature 370, 61(1994)). BODIPY®-α-casein has properties that make it a suitable fluorescent protein substrate for use in fluorescence polarization studies. The method is very rapid and sensitive and eliminates extra manipulations required in most other protease assays. Since fluorescence polarization measurements can be made in the presence of finely particulate matter, such as bacteria, BODIPY®-α-casein can serve as a general substrate for a number of different kinds of microorganisms.

Since proteases may be virulence factors of importance, fluorescence polarization assays performed in real time on small quantities of material, such as a single colony, or small aliquot of culture, or a piece of biopsied material, might immediately distinguish between virulent pathogenic species and less virulent types.

Bolger and Checovich (Bolger B and Checovich W, BioTechniques 17,585–589 (1994)) used FITC-casein to assay proteases at varying pH values by running the protease reaction at the specified pH and then adding 0.2M Tris buffer after 1 hour to bring all the assay tubes to the constant pH of 8.8 for measurement by fluorescence polarization. For their assay a separate tube has to be set up for each time point if one wants to determine kinetics. Using the BODIPY®-α-casein eliminates the extra steps of dilution and switching the pH, allowing one to monitor the reaction in progress and making the gathering of kinetic data extremely convenient.

Among oral anaerobes, pathogenic spirochetes for periodontal diseases include *T. denticola* and black-pigmented *P. gingivalis, Prevotella intermedia* (*Bacteroides intermedius*), *Bacteroides forsythus* and certain species of Capnocytophagia (Seida K, et al, J Periodont Res 27, 86–91 (1992)). Some of the strains of these oral anaerobes show high levels of trypsin-like or other proteolytic activity and can be detected by fluorescence polarization on subgingival plaque samples by assaying for protease activity using a substrate such as α-casein labeled with BODIPY®.

We have shown proteolytic activity associated with certain *T. denticola* and P. gingivalis laboratory strains using using BODIPY®-α-casein (Schade SZ, et al, J Dent Res 74, 54 (1995), abstract #337). We have also shown that the BODIPY®-α-casein fluorescence polarization assay can detect and quantitate considerable proteolytic activity in plaque samples from individual tooth sites (Grys E L, et al, J Dent Res 75, (1996), abstract). In many cases, using only one-tenth the plaque sample from a single site, there is measurable activity in a 5-minute assay (unpublished data). It is expected that we will be able to detect proteolytic activity in samples of gingival crevicular fluid, saliva and other tissues.

With fluorescein-labeled casein, Twining (Twining SS, Anal Biochem 143, 30–34 (1984)) was able to measure proteolytic activity of macrophage extracts using an acid precipitation technique. Macrophage extracts could be assayed more rapidly using BODIPY®-α-casein measuring the decrease in fluorescence polarization.

The sensitivity of fluorescence polarization methodology means that BODIPY®-α-casein can be used to measure enzymes which are available only in limited quantity.

The numbers of enzymes amenable to this technique will be increased. For example the enzymes of certain organelles in cells (such as elastase from PMNs) can be rapidly assayed at its optimum pH of 5, for example. PMN granules occur naturally to have a pH of about 5.

DESCRIPTION OF THE PREFERRED EMBODIMENTS

Having described the invention, the following examples are given to illustrate specific applications of the invention including the best mode now known to perform the invention. These specific examples are not intended to limit the scope of the invention described in this application.

EXAMPLE I

Preparation and suitability of BODIPY®-α-casein for use in fluorescence polarization assays 1. Preparation of BODIPY®-α-casein.

Alpha-casein (Sigma C-7891) at 10 mg per ml was reacted at room temperature with varying concentrations (1 to 0.0001 mg/ml) of 4,4-difluoro-5,7-dimethyl-4-bora-3a, 4a-diaza-s-indacene-3-propionic acid, succinimidyl ester (BODIPY® FL C3-SE, Molecular Probes, Inc.) in 0.1M sodium carbonate buffer at pH 9. Excess BODIPY® was removed by gel filtration in 0.1M phosphate buffer pH 7.0 and the conjugated BODIPY®-α-casein products collected in volumes of 1.5 to 2.0 ml. A stock BODIPY®-α-casein solution was prepared by adding 10 μl of each conjugate to 990 μl of phosphate buffered saline.

2. Rapid protease assays by fluorescence polarization

Twenty pl of stock BODIPY®-α-casein was added to 1.96 ml phosphate-buffered saline or other buffer pre-warmed to 37° C. in a 12×75 mm disposable borosilicate test tube. The final assay volume was 2.00 ml and contained 0.75 μg/ml BODIPY®-α-casein (37 pmol/ml) for assays included in FIG. 1 and Table I. The FPM-1M fluorescence polarization analyzer volley Consulting and Research, Inc.) was used to take fluorescence polarization readings. Readings were automatically recorded in arbitrary milli-polarization units (mP) at 0.5 min intervals. A baseline was established for two minutes and then between two readings, the tube was removed just long enough to add and mix 20 μl of protease (after the 0-minute reading on the graphs). Fluorescence polarization values were recorded for an additional 3 to 5 min.

3. Enzymes

Trypsin (Type I Sigma T-8003) at 0.5 μg/ml was used to test the various conjugates of BODIPY®-α-casein produced, for suitability in fluorescence polarization assays. Chromatographically purified, crystallized pepsin (Sigma P-6887) was used in assays in 0.01 N HCl pH 2.

4. BODIPY®-α-casein characteristics

FIG. 1 presents protease assays measured by fluorescence polarization using trypsin on four different BODIPY®-α-casein conjugates produced with different ratios of BODIPY® reagent to α-casein. Values of fluorescence polarization in millipolarization units (mP) are plotted against time at a gain setting of 80 on the FPM-1™ instrument. Total initial fluorescence values, which were also monitored for additional information, were 743,320; 156,595; 41,675 and 4,366 for conjugates #1, #2, #3 and #4, respectively. The concentration of trypsin present in each assay was 0.5 pg/ml. The initial slopes on the graph (FIG. 1) were identical for the conjugates #2, #3 and #4 and there was a drop in fluorescence polarization in 3 min to 25–30% of the initial value for these three. This result indicates that any one of these three BODIPY®-α-casein products could be used to determine trypsin activity. However, product #3 would be preferred over #2 because of the larger mP change, making the assay more sensitive. Product #3 would be preferred over #4, as well, since the total initial fluorescence of #4 was very low, producing more variability in the readings. Note that product #1 resulting from the reaction with the highest concentration of BODIPY® FL C3-SE was completely unsuitable. The protein was presumably over-labeled creating self-quenching with very low initial fluorescence polarization.

Product #3 also worked well in an assay using pepsin at pH 2. BODIPY®-α-casein conjugate #3 was used at 0.5 μg/ml final concentration in 0.01 N HCl, pH 2 at 37° C. in a 2.00 ml volume. Pepsin stock was prepared at 2 mg/ml and 0.2 mg/ml. The BODIPY®-α-casein was equilibrated in the FPM-1™ instrument for 5 minutes prior to addition of 1 μl of pepsin stock solution.

TABLE I

Protease Assays Using Fluorescence Polarization at pH 2

| Run 1: Final Pepsin 1 μg/ml | | Run 2: Final Pepsin 0.1 μg/ml | |
|---|---|---|---|
| Minutes | Reading(mP) | Minutes | Reading(mP) |
| −1.5 | 191.0 | −1.5 | 191.1 |
| −1.0 | 188.4 | −1.0 | 188.5 |
| −0.5 | 188.0 | −0.5 | 186.8 |
| 0 | 187.4 | 0 | 186.5 |
| ←add pepsin→ | | | |
| 0.5 | 65.1 | 0.5 | 125.9 |
| 1.0 | 50.2 | 1.0 | 97.6 |
| 1.5 | 40.5 | 1.5 | 82.6 |
| 2.0 | 41.0 | 2.0 | 75.1 |
| 2.5 | 39.7 | 2.5 | 70.3 |
| — | — | 3.0 | 65.2 |
| — | — | 3.5 | 61.0 |
| — | — | 4.0 | 58.6 |
| — | — | 4.5 | 57.1 |
| — | — | 5.0 | 56.0 |

In summary, product #3 provided an excellent BODIPY® conjugate for use as a protease substrate in fluorescence polarization assays (using trypsin or pepsin). This conjugate was obtained by reacting 0.01 mg BODIPY® FL C3-SE with 10 mg α-casein in a 1 ml volume (1:1000, BODIPY®:α-casein, FIG. 1).

EXAMPLE II

Assays of known purified enzymes

1. Preparation of optimal BODIPY®-α-casein conjugate

From inspection of the values of the initial total fluorescence of the first four conjugates prepared (EXAMPLE I above), the optimum ratio of reactants for preparing the BODIPY®-α-casein was determined to be 1:500, for BODIPY® FL C3-SE to α-casein, to aim for initial total fluorescence of about 100,000 in the assay. Therefore, a fifth conjugate was prepared. The α-casein was dissolved at 10 mg/ml in 1 ml of 0.1M carbonate-bicarbonate buffer, pH 9.0, and the BODIPY® FL C3-SE was dissolved at 1 mg/ml in 1 ml dimethyl sulfoxide. Twenty μl of the BODIPY® solution (20 μg) was added and mixed with the α-casein solution. After reacting for five minutes at room temperature (22° C.), the excess BODIPY® reagent was removed by passing the solution over a Sephadex G-25 gel filtration column and taken up in 2.0 ml volume. This BODIPY®-α-casein in solution at pH 7 to the eye was a pale pink-orange color with a tinge of yellow-green fluorescence. This conjugate #5 was tested for use in the FPM-1™ fluorescence polarization analyzer at a concentration of 0.5 μg/ml. Trial runs with BODIPY®-α-casein at twice and at half the concentration, 1 μg/ml and 0.25 μg/ml, respectively, gave similar initial rates of proteolysis, indicating substrate saturating conditions desirable for measuring unknown enzyme rates. All assays reported in this patent application subsequent to EXAMPLE I were carried out using this single preparation of BODIPY®-α-casein at 0.5 μg/ml final concentration.

2. Storage and stability of BODIPY®-α-casein

The conjugate was stored frozen at −70° C. in 10 μl aliquots (5 mg/ml) in polypropylene microtubes. These aliquots have been stable at −70° C. for 12 months with no loss in initial fluorescence nor ability to serve as protease substrates. For use in fluorescence polarization assays, the 10 pl of conjugate was diluted with 0.99 ml ice-cold phosphate-buffered saline containing 0.02% sodium azide pH 7.4 (PBS-azide) to prepare a working stock substrate. The working stock BODIPY®-α-casein solution was kept on ice until addition to assay buffer. Twenty μl was included in a final 2.0 ml assay volume. The stock could be frozen and thawed for subsequent assays with only slight changes in fluorescence polarization properties. For assays to be conducted at other pH values, the stock solution was made up in buffer at the pH required and used only for that day's experiments.

3. Sources of known purified proteolytic enzymes

Chromatographically purified, crystallized pepsin (Sigma P-6887) was used in assays in 0.01N HCl pH 2. Papain (Sigma P-3125) was activated by adding 35 pl of the suspension to 900 pl 0.1M citrate buffer pH 6 containing 1.1 mM EDTA, 0.067 mM 2-mercaptoethanol and 5.5 mM L-cysteine. This suspension of 1 mg/ml (24 units/ml) papain was allowed to stand 30 min at 20° C., afterwhich it was kept on ice. It was active in assays in 0.1M citrate buffer at both pH 5 and 6. Proteinase K (Amresco 0706C) and trypsin (Type I, Sigma T-8003) were used in phosphate-buffered saline pH 7.4 containing 0.02% sodium azide. Alkaline protease from *Streptomyces griseus* (Type XXI, Sigma P-0652) was used in assays in 0.1M CAPS buffer at pH 11.

4. Results with known proteases at different pH values

To test the BODIPY®-α-casein conjugate #5 as a protease substrate at different pH values, five purified enzymes were chosen with varying pH optima and assayed for activity at or near their optimal pH values (FIGS. 2, 3, 4, 5 and 6). Different buffers were necessary to obtain the optimum pH for each of the enzymes tested. For BODIPY®-α-casein product #5, the initial fluorescence polarization values observed in the different buffers were nearly the same, although the pH values ranged from pH 2 to 11. The initial fluorescence polarization values measured in mP units were 180, 220, 200 and 210 for BODIPY®-α-casein in 0.01N HCl pH 2.0, 0.1M citrate pH 6.0, PBS-azide pH 7.4, and 0.1M CAPS buffer pH 11, respectively.

In each case, BODIPY®-α-casein was cleaved by the respective enzyme, as evidenced by the drop in mP value. If no protease was added, no change in fluorescence polarization occurred. The rate of change in mP was dependent upon the concentration of enzyme in all cases.

Figure 2:
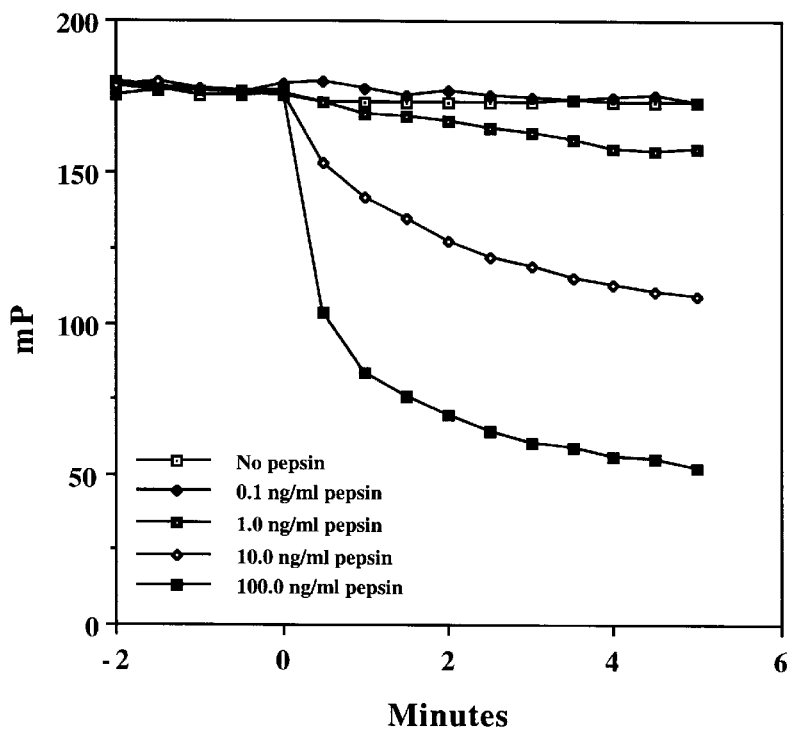
Figure 3:
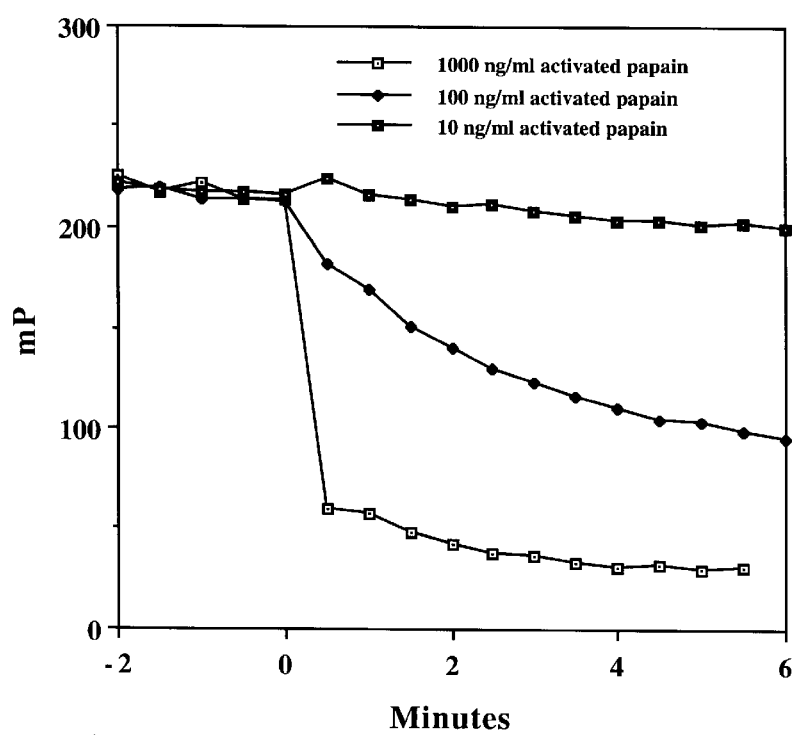
Figure 4:
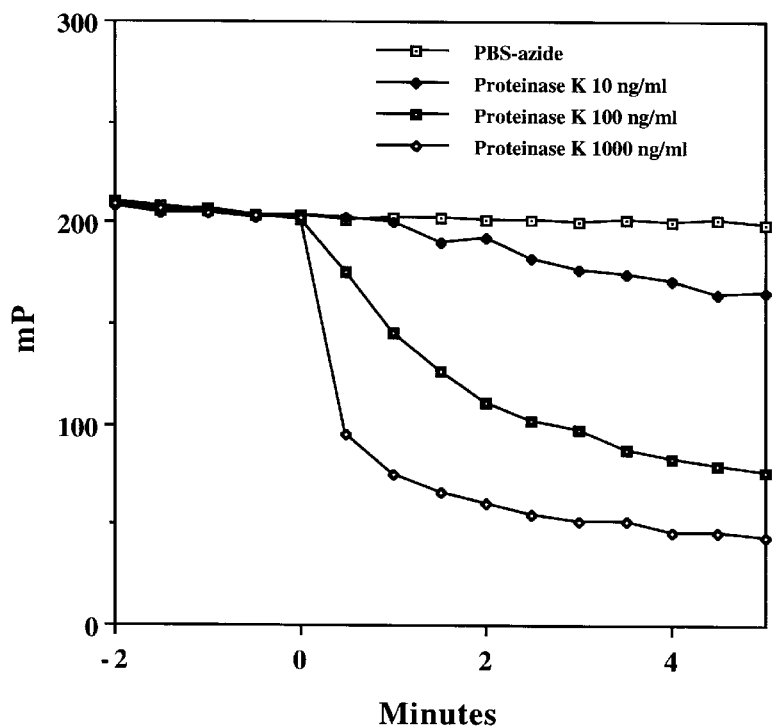
Figure 5:
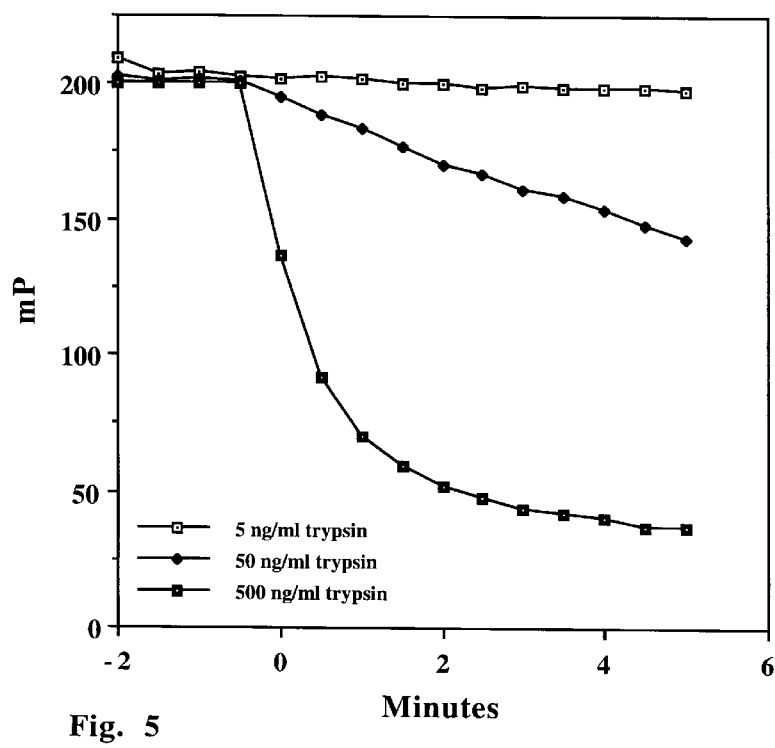
Figure 6:
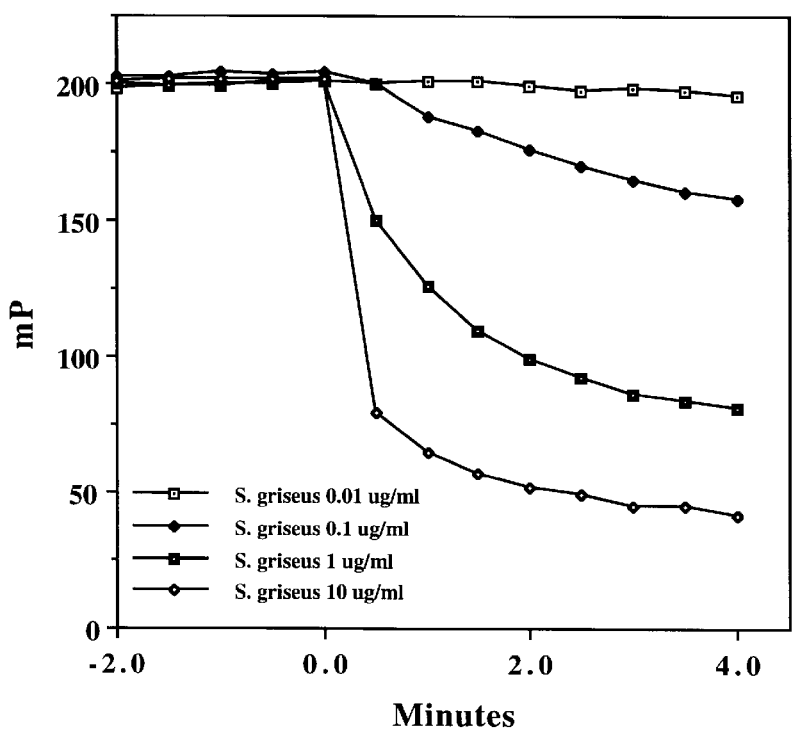

The BODIPY®-α-casein was cleaved by pepsin in 3 minutes at a sensitivity of 1 ng/ml (4 milliunits/ml) at pH 2 (FIG. 2). It was cleaved by activated papain in 3 minutes at a sensitivity of 20 ng/ml (0.5 milliunits/ml) at pH 6 (FIG. 3). It was cleaved by proteinase K in 3 min at a sensitivity of 10 ng/ml (0.3 milliunits/ml) at pH 7.4 (FIG. 4). It was cleaved by trypsin in 3 minutes at a sensitivity of 5 ng/ml (50 milliunits/ml) at pH 7.4 (FIG. 5). It was cleaved by *S. griseus* alkaline protease in 3 minutes at a sensitivity of 50 ng/ml (1 milliunit/ml) at pH 11 (FIG. 6).

At all pH values, when the appropriate protease was used at about 100 times these concentrations [0.1 μg/ml for pepsin (FIG. 2), 1 μg/ml for papain (FIG. 3), 1 pg/ml for proteinase K (FIG. 4), 0.5 μg/ml for trypsin (FIG. 5), or 10 μg/ml for *S. griseus* alkaline protease (FIG. 6)], there was an immediate change in fluorescence polarization, falling to near the theoretical low limit within two to five minutes.

This drop in fluorescence polarization of approximately 150 mP units in the presence of proteolytic enzymes, together with the fact that the fluorescence of the BODIPY® ligand is independent of pH, makes the BODIPY®-α-casein an excellent substrate for use in fluorescence polarization studies over a wide range of pH values from about pH 2 to 11.

5. Dependence of proteolytic activity of papain upon pH

Figure 7:
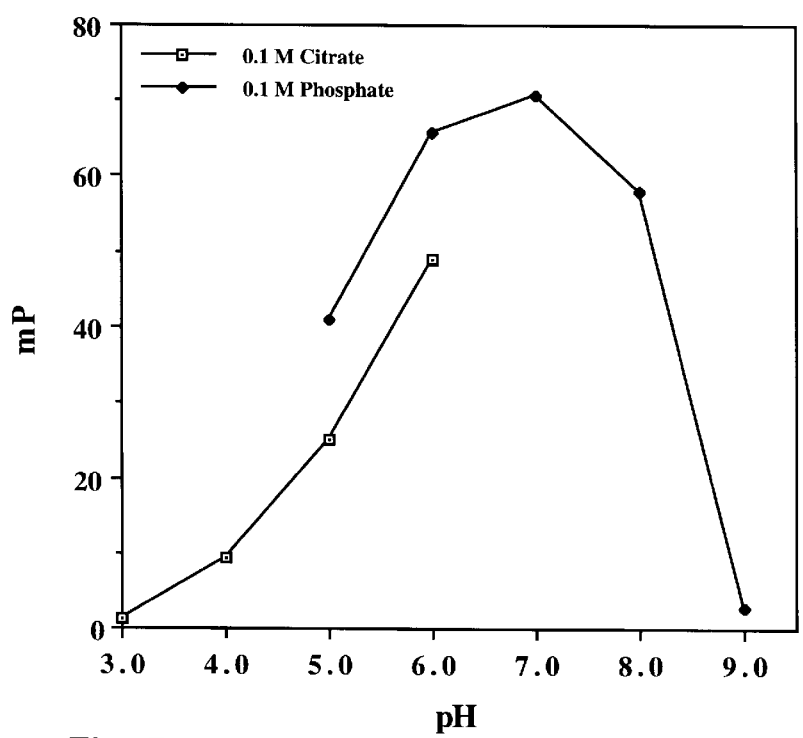

Each purified enzyme has an optimum pH range for activity as mentioned above. To test whether fluorescence polarization technology would be appropriate to determine pH optima of enzymes, the enzyme papain was selected and its proteolytic activity was measured at 37° C. against BODIPY®-α-casein at pH 3, 4, 5, and 6 using 0.1M citrate buffers and at pH 6, 7, 8 and 9 using 0.1M sodium phosphate buffers. The results are presented in FIG. 7. Each point in this figure is derived from a kinetic curve run in a similar way to those in the previous graphs. The initial enzyme velocity, measured as the decrease in mP during the first minute after addition of the papain, is plotted against the pH used for the kinetic assay. The quantity of enzyme added was the same at each pH. The citrate and phosphate curves were assayed on different days with a different batch of activated papain, which may account for the discrepancy at pH 6. However, different buffers are often found to exert these kind of effects. The pH profile is strikingly similar to published pH dependence profiles obtained for papain using two different short synthetic substrates: 2.5 mM benzoyl-glycine ethyl ester at 25° C. (Sluyterman LAAE and deGraaf J M, Biochim Biophys Acta 258, 554–561 (1972)) or 25 mM α-benzoyl-L-argininamide at 38° C. (Stockell A and Smith E L, J Biol Chem 227, 1–26 (1957)).

EXAMPLE III

Assays for bacterial proteases

All bacteria have several proteases that function as "housekeeping" enzymes to run common metabolic tasks within the cells, but in addition to these, some pathogenic bacteria elaborate potent surface-associated or extracellular proteases. To be able to quickly test for these potent proteolytic activities would be clinically useful.

1. Bacteria

*T. denticola* and *Treponema phagedenis* were grown under anaerobic conditions in mycoplasma broth or spirolate medium containing sodium bicarbonate and 10% fetal calf serum or rabbit serum. *P. gingivalis* was cultured in Wilkin-Chalgren broth supplemented with hemin and menadione.

2. Assays for bacterial proteases in the presence of the bacteria.

Kinetic assays using the fluorescence polarization analyzer, FPM-1™, can be carried out in either of two ways. The reagents are identical but the order of addition of reagents is reversed in one compared to the other. In EXAMPLE I and II above, BODIPY®-α-casein substrate was added to buffer and readings taken for two minutes in the FPM-1™ prior to addition of enzyme. When bacterial suspensions were assayed for protease activity, 1 to 20 μl of whole culture or washed bacteria carrying the enzyme activity was added first to the assay buffer (volume adjusted for final assay volume of 2.00 ml). Then a reading was taken to assess whether excessive fluorescence was introduced by the culture medium or wash buffer. The reaction was begun by the addition of 20 μl BODIPY®-α-casein substrate and readings taken at 0.5-minute intervals. In this case, change in fluorescence polarization was determined by comparison with an assay of the same volume of culture medium alone. Various culture media gave either minimal or no change in fluorescence polarization.

3. Results

Figure 8:
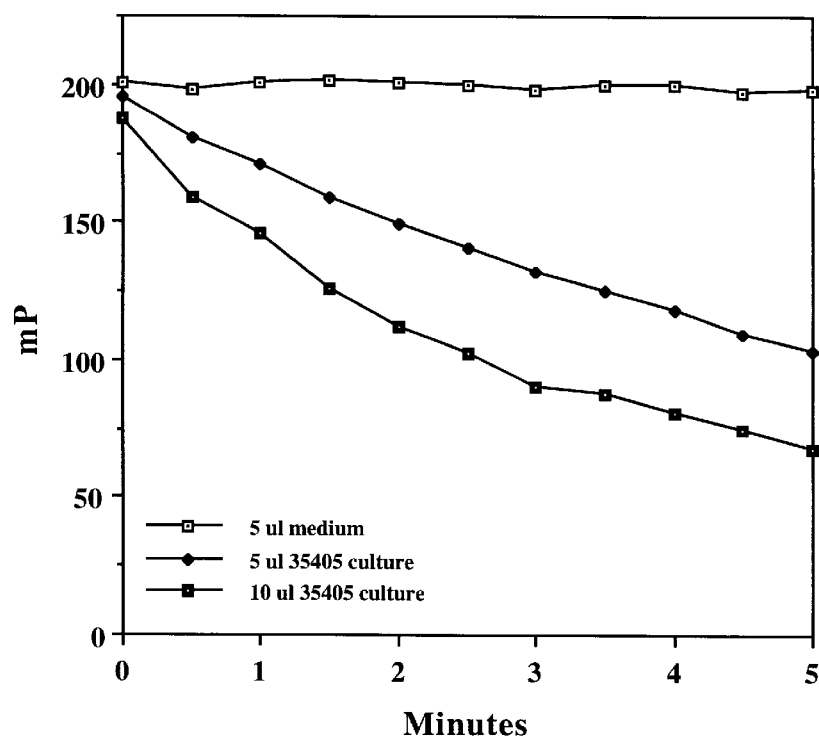

FIG. 8 shows representative protease assays on two samples of a culture of T. denticola bacteria in PBS-azide pH 7.4 at 37° C. using BODIPY®-α-casein and measured by fluorescence polarization. Twice the quantity of bacteria produced twice the initial slope on the graphs showing the dependence of the change in fluorescence polarization upon the number of bacteria. If the bacteria were washed by centrifugation, the major portion of the activity remained with the bacteria (results not shown). No protease activity was observed with uninoculated medium (FIG. 8).

Figure 9:
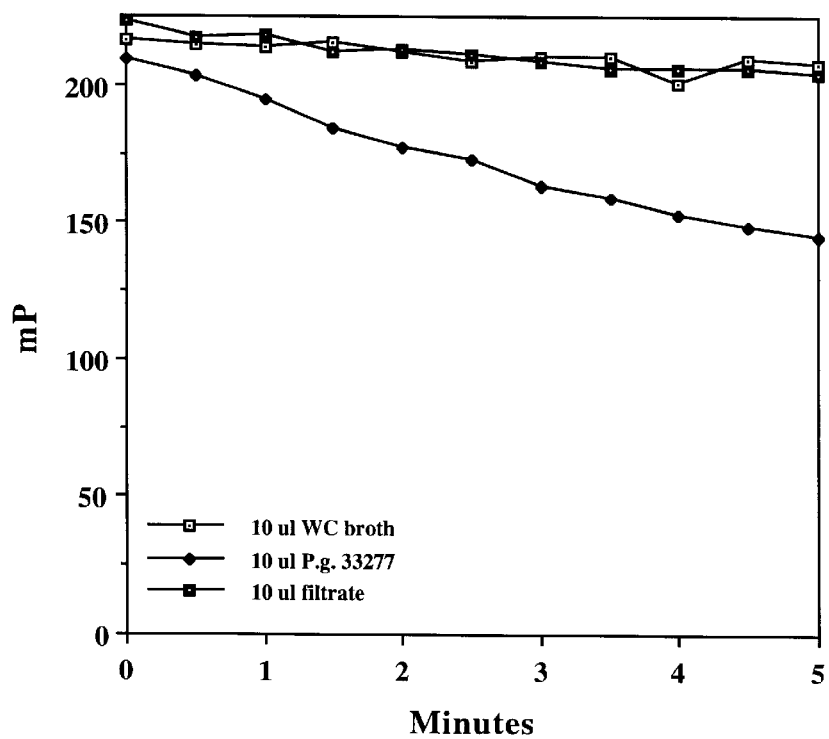

A culture of a different species of bacteria, P. gingivalis, was assayed for proteolytic activity using BODIPY®-α-casein and measured by fluorescence polarization (FIG. 9). If the bacteria from a 1-day rapidly growing culture were filtered out of the medium, using an Acrodisc® (Gelman) filter of 0.2 μm pore size with low-protein binding characteristics, there was no activity left in the medium (FIG. 9), indicating that the protease activity was bacterial associated. In this case only ten pl of culture was necessary to show marked protease activity in a few minutes. With older cultures, it required only one μl of culture.

4. Inhibition of proteolytic activity

Heating a culture of T. denticola at 60° C. for 2 or 4 hours eliminated 70% and 100% of the proteolytic activity, respectively, measured at pH 7.4. Mercuric ion at 1 micromolar concentration in the assay buffer also decreased the activity by 80%. A serine protease inhibitor, Pefabloc® SC (Pentapharm Ltd, Basel), at 1 mg/ml completely inhibited T. denticola protease activity. These results help establish that the change in fluorescence polarization measures true enzyme activity and that it is not an artifact of the method. Fluorescence polarization assays would be useful in studying inhibition of enzyme activities.

Previously, we tested several laboratory strains of oral microorganisms for proteolytic activity using commercially available fluorescein-α-casein (FITC-casein) in fluorescence polarization assays (Schade S Z, et al, J Dent Res 73,248 (1994), abstract # 1168). We have presently used BODIPY®-α-casein to test for protease activity on some of the same strains of T. denticola, on T. phagedenis and on several strains of P. gingivalis. Table II presents values for the change in fluorescence polarization under the same conditions either with BODIPY®-α-casein or with FITC-α-casein as substrate on identical quantities carried out on the same day with the same cultures of different bacterial strains.

TABLE II

Protease activity of bacterial cultures at 37° C. using BODIPY ® -α-casein or FITC-α-casein as substrate in fluorescence polarization assays.

| Strain | BODIPY ® -α-casein | FITC-α-casein |
|---|---|---|
| P. gingivalis | | |
| JKG-1 | 68.4* | 32.8* |
| JKG-7 | 30.7 | 6.9 |
| D13B11 | 34.8 | 19.3 |
| D67D9 | 62.5 | 43.7 |
| D86B6 | 94.7 | 62.2 |
| ATCC 33277 | 19.3 | 15.5 |
| A7436 | 29.4 | 17.1 |
| T. denticola | | |
| ATCC 35405 | 89.0 | 50.8 |
| GM-1 | 96.2 | 79.5 |

TABLE II-continued

Protease activity of bacterial cultures at 37° C. using BODIPY ® -α-casein or FITC-α-casein as substrate in fluorescence polarization assays.

| Strain | BODIPY ® -α-casein | FITC-α-casein |
|---|---|---|
| D39DP1 | 59.1 | 33.6 |
| ATCC 33521 | −1.7** | 2.0** |
| T. phagedenis | 1.7** | −0.6** |

*Decrease in mP in first 2 minutes
**Not significantly different from background.

The P. gingivalis strains, T. denticola strains and T. phagedenis all showed the same pattern of proteolytic activity using BODIPY®-α-casein as they showed using FITC-α-casein. The T. phagedenis strain showed no proteolytic activity with either substrate and is known to lack extracellular proteases. The absence of activity in T. denticola ATCC 33521 may be due to long passage of this culture under laboratory conditions. The bacteria are still spirochetes under darkfield microscopy and still react to monoclonal antibody produced against earlier passages of this strain. Another possibility would be that the protease genes of this strain are inducible and that, under the growth conditions used, the genes are turned off. The data suggest that BODIPY®-α-casein is as good a substrate, if not better, for assays of bacterial proteases as the commercially available FITC-α-casein using fluorescence polarization methodology at pH 7.4. However, for species of bacteria which thrive in or tolerate an acid environment, a BODIPY®-labeled substrate would be necessary.

The BODIPY®-α-casein was used to determine if the T. denticola proteases were active under various pH conditions. Table III presents results on equal quantities of a culture of T. denticola ATCC 35405 assayed for proteolytic activity with BODIPY®-α-casein from pH 2.5 to pH 10. The BODIPY®-α-casein was stable at all pH values during the assay time period, showing no change in fluorescence polarization at any pH in the presence of culture medium alone.

TABLE III

Proteolytic activity of Treponema denticola ATCC 35405 at different pH values, assayed by fluorescence polarization at 37° C., using BODIPY ® -α-casein as substrate.

| Buffer | pH | ΔmP |
|---|---|---|
| Citrate, 0.2 M | 2.5 | 13.2* |
|  | 4 | 28.3 |
|  | 5 | 42.6 |
|  | 6 | 46.4 |
| HEPES, 0.2 M | 7 | 44.9 |
|  | 8 | 46.1 |
| Carbonate, 0.2 M | 9 | 60.0 |
|  | 10 | 46.3 |
|  | 11 | 44.1 |

*Decrease in fluorescence polarization in 2 minutes

The data reflect the sum of various proteases in a growing culture of T. denticola. Buffers of 0.2M were used since Rosen, et al (Rosen G, et al, Infect & Immun 62, 1749–1754 (1994)) reported highest activities for isolated proteolytic enzymes of T. denticola at 0.2M. The data suggest that the proteases of T. denticola ATCC 35405 were active over a wide range of pH conditions from pH 5 to pH 11, with diminution at pH 2.5 and pH 4.

EXAMPLE IV

Protease assays on dental plaque

1. Collection of dental plaque.

Subgingival dental plaque was removed separately from six different teeth of both healthy and patients with periodontitis (208 individual plaque samples) by Northwestern University Dental School dental personnel experienced in the practice of periodontal treatment. The total subgingival plaque from each site was placed into 200 µl of cold saline containing 20 mM $MgCl_2$ and 3–4 glass beads and frozen. After thawing, the samples were vortexed to disperse the sample and 20 µl assayed for proteolytic activity using BODIPY®-α-casein at 37° C. in PBS-azide pH 7.4 in a final volume of 2.00 ml.

2. Assays on dental plaque

Proteolytic assays using BODIPY®-α-casein and fluorescence polarization have been performed on both supragingival and subgingival dental plaque samples and saliva. On one healthy subject, only the subgingival plaque showed substantial activity, which is the niche where the anaerobic, protease-forming bacteria reside. Periodontitis patients showed variable subgingival plaque proteolytic activity among 6 sites tested from each patient. Fluorescence polarization protease assays detected significant protease activity in 5 minutes in 87 of 208 individual plaque samples. Periodontal patients had significantly greater numbers of sites with subgingival plaque that showed proteolytic activity and had quantitatively higher values per site that showed proteolytic activity than healthy patients.

It required only one-tenth the total plaque sample from each tooth site to determine proteolytic activity in a 5-minute assay by this method. It is our goal to determine whether subgingival plaque proteolytic activity correlates with clinical evidence of periodontal disease upon a larger number of patients using this rapid method. Since plaque is 99% bacterial in composition, one can deduce the enzyme activity is derived from the bacteria. If high levels of proteolytic activity are present, there is a good indication that one or more of about ten specific strains of bacteria are present among an estimated 350 that have been cultivated from the mouth to date (Seida K, et al, J Periodont Res 27, 86–91 (1992)).

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

What is claimed is:

1. A method for determining enzymatic activity in a sample comprising intermixing with said sample a labeled substrate comprising a substrate for said enzyme conjugated with a derivative of 4,4-difluoro-5,7-dimethyl-4-bora-3a,4a-diaza-s-indacene and determining the change in the amount of fluorescence polarization at pH values at the ends of the pH spectrum from most acid pH between pH2 and pH5, to most basic pH between pH 8 and pH 11 and the determination followed in real-time at that pH as a measure of the amount of enzyme in the sample.

2. The method according to claim 1 wherein the fluorescence polarization is conducted at a pH from pH 2 to pH 5.

3. The method according to claim 2 wherein the derivative of 4,4-difluoro-5,7-dimethyl-4-bora-3a,4a-diaza-s-indacene is 4,4-difluoro-5,7-dimethyl-4-bora-3a,4a-diaza-s-indacene-3-propionic acid, succinimidyl ester.

4. The method according to claim 3 wherein the enzyme is a proteolytic enzyme.

5. The method according to claim 4 wherein the substrate is a protein.

6. The method according to claim 5 wherein the protein is α-casein.

7. A method for determining enzyme-producing bacteria in a sample comprising determining the enzymatic activity produced by the bacteria comprising: intermixing with said sample a labeled substrate comprising a substrate for said enzyme conjugated with a derivative of 4,4-difluoro-5,7-dimethyl4-bora-3a,4a-diaza-s-indacene and determining the change in fluorescence polarization at one or more different pH values at the ends of the pH spectrum from most acid pH between pH2 and pH5,, to most basic pH between pH 8 and pH 11 and the determination followed in real-time at that pH as a measure of the amount of enzymatic activity in the sample; and correlating the amount of enzymatic activity with the amount of enzyme in the sample and with the presence or amount of bacteria in the sample.

8. The method according to claim 7 wherein the derivative of 4,4-difluoro-5,7-dimethyl-4-bora-3a,4a-diaza-s-indacene is 4,4-difluoro-5,7-dimethyl-4-bora-3a,4a-diaza-s-indacene-propionic acid, succinimidyl ester.

9. The method according to claim 8 wherein the fluorescence polarization is conducted at any pH from pH 1 to pH 13.

10. The method according to claim 9 wherein the enzyme is a proteolytic enzyme.

11. The method according to claim 10 wherein the substrate is a protein.

12. The method according to claim 11 wherein the protein is α-casein.

* * * * *